(12) United States Patent
Sartorius et al.

(10) Patent No.: US 9,103,774 B2
(45) Date of Patent: Aug. 11, 2015

(54) METHOD AND DEVICE FOR IDENTIFYING A MATERIAL

(75) Inventors: Bernd Sartorius, Berlin (DE); Helmut Roehle, Berlin (DE); Dennis Stanze, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 548 days.

(21) Appl. No.: 13/504,239

(22) PCT Filed: Oct. 25, 2010

(86) PCT No.: PCT/EP2010/006590
§ 371 (c)(1),
(2), (4) Date: May 14, 2012

(87) PCT Pub. No.: WO2011/050959
PCT Pub. Date: May 5, 2011

(65) Prior Publication Data
US 2012/0217403 A1     Aug. 30, 2012

(30) Foreign Application Priority Data
Oct. 27, 2009   (DE) .......................... 10 2009 051 692

(51) Int. Cl.
*G01J 5/02*     (2006.01)
*G01N 21/3581*  (2014.01)
(Continued)

(52) U.S. Cl.
CPC ........ *G01N 21/3581* (2013.01); *G01N 21/3563* (2013.01); *G01N 21/90* (2013.01)

(58) Field of Classification Search
CPC ...................................................... G01N 21/35
USPC ................................................... 250/339.12
See application file for complete search history.

(56) References Cited

U.S. PATENT DOCUMENTS 6,957,099 B1   10/2005  Arnone et al.
2004/0061055 A1*  4/2004  Kawase et al. ................ 250/330
(Continued)

FOREIGN PATENT DOCUMENTS

DE   102007011820 A1   9/2008
WO   WO0106915 A1      2/2001

OTHER PUBLICATIONS

Ikeda, Takeshi et al., "Investigation of inflammable liquids by terahertz spectroscopy", Applied Physics letters, vol. 87, No. 3, Jul. 14, 2005, 3 pages.
(Continued)

*Primary Examiner* — David Porta
*Assistant Examiner* — Meenakshi Sahu
(74) *Attorney, Agent, or Firm* — Faegre Baker Daniels LLP

(57) ABSTRACT

A material may be identified using THz radiation that simultaneously or sequentially includes at least one first frequency portion and a second frequency portion different therefrom. An object formed from the material to be identified is irradiated with the THz radiation and the THz radiation exiting the object is detected using a phase-sensitive THz receiver. A time or phase offset, caused by the object, is measured at least for the first frequency portion and a material thickness is determined therefrom. Attenuation of the received signal, at least for the second frequency portion, is determined. An absorption coefficient for at least the second frequency portion is calculated using the material thickness.

23 Claims, 2 Drawing Sheets

(51) Int. Cl.
*G01N 21/90* (2006.01)
*G01N 21/3563* (2014.01)

(56) References Cited

U.S. PATENT DOCUMENTS

2004/0155665 A1 8/2004 Arnone et al.
2007/0282206 A1* 12/2007 Arnone et al. ............... 600/473

OTHER PUBLICATIONS

International Search Report and Written Opinion issued in PCT/EP2010/006590, mailed Mar. 22, 2011, 10 pages.

Matton, S. et al., "Generation and coherent detection of terahertz radiation by photomixing: dielectric media characterization", Spectroscopy and Material Properties, 2005 Joint 30th Int. Conf. on Infrared and Millimeter Waves and 13th Int. Conf. on Terahertz Electronics, vol. 2, Sep. 19, 2005 and Sep. 23, 2005, pp. 419-420.

Mouret, G. et al., "THz medial characterization by means of coherent homodyne detection, results and potential applications", Applied Physics B., Lasers and Optics, vol. 89, No. 2-3, Oct. 3, 2007, pp. 395-399.

Wietzke, S. et al., "Applications of terahertz spectroscopy in the plastics industry" proceedings of the SPIE Terahertz Photonics, vol. 6840, 2007, pp. 1-9.

* cited by examiner

METHOD AND DEVICE FOR IDENTIFYING A MATERIAL

RELATED APPLICATIONS

This application is a national phase application of PCT/EP2010/006590, internationally filed on Oct. 25, 2010, and is filed pursuant to 35 U.S.C. §371, which application claims priority to German Application No. 10 2009 051 692.1, filed Oct. 27, 2009. Both applications are incorporated by reference in their entirety.

TECHNICAL FIELD

The invention relates to a method for identifying a material from a class of materials which are transparent to THz radiation.

BACKGROUND

Plastics are increasingly used as a material for packaging, vessels or other products of a relatively short serviceable life, so that more and more corresponding waste arises. It is desirable to lead this waste to a recycling chain for various reasons. Firstly, it is in the interest of the protection of the environment to minimize waste and in particular to sort away materials which are harmful to the environment. On the other hand it makes economic sense to recycle valuable material.

A first step in a recycling chain is to recognize the different substances, in order to then be able to lead them to the correct recycling processes. Methods for automatically identifying different plastic types for this purpose have not yet established themselves. For example, in order to ascertain from which sort of plastic the empty containers are manufactured, these until now had to be characterized accordingly, for example with the aid of a barcode.

SUMMARY

The present invention provides a method and a corresponding device which allows plastics, and, if possible also other materials, to be automatically identified or at least assigned to a limited class of substances, wherein the device should be constructed as simply as possible and wherein the method should be able to be implemented in a quick and simple manner, and, if possible, without contact, and not be dependent on a characterization of the objects to be examined.

Thus what is suggested in a method of identifying a material from a class of materials which are transparent to THz radiation, with which THz radiation is produced by a THZ emitter, said THz radiation containing at least one first frequency component and a second frequency component of a wavelength which is different to this, wherein this THz radiation is beamed through an object which is at least partly formed from the material to be identified, and the THz radiation which exits from the object is detected with a phase-sensitive THz receiver, wherein moreover at least for the first frequency component, a time shift or phase shift of a receive signal produced by the THz radiation in the THz receiver, said shift being caused by an object, is further measured, from which signal at least approximately a measure of the material thickness of the object is determined, and wherein at least for the second frequency component, a damping of the receive signal which is caused by the object is determined, from which damping an absorption coefficient for at least this second frequency component is computed amid the use of the determined measure for the material thickness. With regard to the examined object, it can for example be the case of an empty container, such as e.g. a bottle or also another vessel, wherein the mentioned material can in particular be plastic, since plastic is transparent to THz radiation. As used herein THz radiation refers to as electromagnetic waves of a frequency of between 50 GHz and 10 THz.

It is insignificant as to whether the frequency components are irradiated at the same time or sequentially. The THz radiation thus can contain these frequency components simultaneously as spectral components or also as components which are temporally successive to one another. For determining the damping or weakening and the time shift or phase shift, apart from a power or amplitude, a time position or a phase is also determined when detecting the THz radiation with the phase-sensitive THz receiver.

In some embodiments, the phase-sensitive THz receiver can be synchronized with the THz emitter, for example via a synchronization connection between the THz radiation emitter and the THz receiver. A stable common time base for the detection of the time position or phase of the THz radiation can be ensured by way of such a synchronization function.

The use of THz radiation thereby firstly entails the advantage that plastics, also colored plastic materials, and paper are transparent to radiation from the mentioned spectral region, in particular for THz radiation of a frequency of up to about 3 THz. With the suggested methods, thus e.g. colored bottles and those which are provided with labels can be examined. With the examination of plastic materials however, it has been found that these in the THz spectral region have no characteristic absorption lines whose frequencies or wavelengths can be used for identification as is common in classic spectroscopy. With the claimed invention, a possibility is suggested as to how absorption characteristics in the THz spectral region which are typical for plastics can be used for material identification, even without sharp absorption lines. Thereby, one utilizes the fact that plastics and other materials which are transparent to THz radiation, even if they have no sharp THz absorption lines, display a different intensity of absorption for THz radiation THz waves of a different frequency. Thereby, this absorption or an absorption coefficient describing this absorption typically rises in a gradual manner with an increasing frequency, wherein different materials differ from one another by way of different values and gradients of their absorption coefficient for THz radiation. For this reason, by way of the magnitude of absorption of THz radiation in a material, one can obtain information with regard to what sort of material it is. Since however a product of material thickness and absorption coefficient is included in the absorption, for this one must also determine the material thickness in an as accurate as possible manner. With the suggested method, this is effected by way of the time shift or the phase shift of the receive signal produced by THz radiation in the THz receiver and caused by the object to be examined, being measured at least for the first of at least two applied frequency components. This time shift or phase shift, assuming a refractive index which is typical for the mentioned class of materials, can at least approximately serve as a measure for the material thickness or for determining such a measure for the material thickness. Thus the refractive indices of the different plastics typically lie in the region between 1.5 and 1.75, so that e.g. the assumption of an average value of n=1.62 permits the evaluation of the material thickness with an error of less than 10% even without knowledge of the material. Thereby, the material thickness indicted hereinafter at d, can be determined according to $$d = \Delta t \cdot c/(n-1),$$

wherein Δt is the measured time shift, c is the vacuum speed of light and n is the assumed refractive index. By way of then determining a damping of the receive signal caused by an object, at least for the second frequency component, then amid the use of this damping and the determined measure for the material thickness, one can compute an absorption coefficient of the material to be identified, for at least this second frequency component, which permits this material to be deduced or at least to be assigned to a limited group of materials concerned.

Thus advantageously, in particular one can identify plastic materials, even of the objects manufactured of these plastic materials have no characterization indicating the material, for example in the form of a barcode. With regard to these objects to be examined, it is the case e.g. of drinks bottles, shampoo bottles, plastic beakers or other vessels for household products. Thereby, it does no harm if these objects are additionally provided with labels or are colored.

Due to the fact that the applied THz radiation includes at least two different frequency components, a wavelength of the first frequency component can advantageously be selected large enough that the phase shift caused by the object can permit the material thickness to be unambiguously deduced, whereas an absorption in the material to be identified is still so low for this wavelength, that the phase shift is particularly simple to measure. Simultaneously, on account of this, the wavelength of the second frequency component can be selected smaller than the wavelength of the first frequency component, so that the absorption coefficients of different materials differ significantly for this second frequency component. Thus e.g. the first frequency component can be selected such that it contains electromagnetic waves with a frequencies between 50 GHz and 200 GHz, for which most of the materials concerned still display a very low absorption, while the second frequency component can be selected such that it contains electromagnetic waves with frequencies of e.g. between 0.5 THz and 4 THz, or between 0.5 THz and 2.5 THz. In some embodiments, a wavelength of the first frequency component is selected at least as large as a wall thickness of the object, which with a refractive index of the magnitude of n=1.5 and taking into account the fact that with the method one typically beams through two walls of the object and the material thickness corresponds to twice the wall thickness, leads to the measured phase shift allowing the deduction of the material thickness without any ambiguities.

One advantageous device, with which the method described here can be carried out and with which it can e.g. be the case of a reverse vending machine for empties or waste to be led to a recycling process, accordingly includes a THz emitter for producing THz radiation with at least one first frequency component and a second frequency component of a wavelength different from the first frequency component, a phase-sensitive THz receiver for detecting the THz radiation and an evaluation unit. Thereby, the evaluation unit is set up to measure a time shift or phase shift of a receive signal produced by the THz radiation in the THz receiver, at least for the first frequency component, and for determining an amplitude of the receive signal or at least a component of the receive signal which corresponds to the second frequency component, wherein the evaluation unit by way of programming technology is further set up to determine a measure for a material thickness of a beamed-through object from the time shift or phase shift, and to determine a damping of the receive signal which is caused by the object, from the measured amplitude and to compute an absorption coefficient amid the use of the determined measure for the material thickness. The time shift for which the evaluation unit is set up to measure, thereby is to indicate a change of a delay of the receive signal with regard to the THz radiation emitted by the THz emitter and which with the correct use of the device is caused by an object which is to be examined with regard to its material and which for this is brought into the beam path of the device.

The phase-sensitive THz receiver is thereby not only suitable for determining a power or amplitude, but also a time position or phase. The mentioned time shift or phase shift of the receive signal thereby indicates a time shift or phase shift with respect to a comparison signal which is produced in the receiver when the examined object is not located in the beam path between the THz emitter and the phase-sensitive THz receiver. The time shift or phase shift can thus e.g. be measured by way of comparing the receive signal with a comparison signal produced with a comparative measurement without the object being beamed through.

Damping is to be understood as a weakening of the receive signal by the beamed-through object, said weakening being able to be determined by a comparison of the measured power with a comparison power value which is determined with a comparative measurement without the object being beamed-through. In the simplest case, the absorption coefficient can be determined by way of the relation $$P=P_0 \cdot \exp(-d \cdot a)$$

if P indicates the measured power, $P_0$ the comparison power value, d the material thickness and a the absorption coefficient. Additionally to the absorption, reflection losses can however also be included in the damping, which under certain circumstances are computed by computation or can be eliminated by way of subtracting frequency-dependent components of the damping or absorption.

Additionally, the evaluation unit by way of programming technology can advantageously be set up to compare the computed absorption coefficient or a variable derived therefrom, e.g. a frequency-dependent component of the absorption coefficient, with comparison values and to assign the beamed-through object to a material or to a group of possible materials, if the absorption coefficient or the variable derived therefrom falls into an interval which is assigned to the material or to the group of materials.

Moreover, the evaluation unit can also be set up to carry out the further method steps which serve for an evaluation of the measurement results and an assignment or identification of the material and which here are described in combination with advantageous developments of the method.

The material, from which the beamed-through object is at least partly and typically mainly formed, can thus be identified or be assigned to a group of possible materials by way of the computed absorption coefficient or a frequency-dependent component of the absorption coefficient determined therefrom being compared to comparison values. The latter can be stored in a data bank. Thereby, different intervals for allowable damping or absorption coefficients can be defined for different materials, wherein the decision as which material it is a case of or to which group of possible materials the material is to be assigned can then be made depending on in which of the intervals the experimentally determined absorption coefficients fall. Reflection losses can thereby be taken into account with the determining of the absorption coefficients, be it by computation, for example by way of determining a reflection rate R by way of the formula $$R=(n-1)^2/(n+1)^2,$$

or be it for example by way of a comparative measurement carried out for the first frequency component, at a different wavelength.

A preliminary decision or a supplementary decision can be made with regard to which materials or groups of materials or to which types of objects are considered for the object, depending on measure for the material thickness which is determined by way of the measured time shift or phase shift. For this, intervals for material thicknesses which are to be considered for certain materials or types of objects can be stored in the data bank. Thus for example when examining empty containers, one can assume that a bottle of glass has a wall thickness of between 3 mm and 6 mm. With bottles for shampoo or washing-up liquid, an as cheap as possible material is selected, for example HDPE and wall thicknesses of approx 1 mm are common. For foodstuffs, however, taste neutrality and foodstuff suitability are absolutely necessary. The material choice here is PET which however is expensive and therefore is used with an as thin as possible wall thickness. Thicknesses of about 0.3 mm for disposable bottles and approx. 0.6 mm for returnable bottles are common.

In one advantageous development of the method, the time shift or phase shift of the receive signal is not only measured for the first frequency component, but also for the second frequency component and is suitably evaluated for a more precise evaluation of the thickness. Moreover, it is advantageous if the damping or the absorption of the receive signal again is not only determined for the second frequency component, but also for the first frequency component and suitably evaluated, so that a typically frequency-independent part of the damping or absorption, which originate from unspecific losses, can be recognized and computed out. Such unspecific losses can be caused e.g. by the scattering of color pigments, by contamination or by way of a surface roughness. A frequency-dependent part of the damping or absorption can form the basis of the further analysis and e.g. can be determined by way of obtaining the difference between the damping or absorption coefficients which are determined for the different wavelengths or frequency components. An influence of unspecific losses which is independent of the material to be identified, be it on surfaces due to reflection, be it due to scatter on roughness or contamination, can thus be very accurately detected and eliminated in the described manner. By way of this results a method, with which a material thickness as well as an absorption of THz radiation caused by material can be determined in a quick, simple and contact-free manner and simultaneously disturbing background losses can be detected such that a share of the absorption which is due to the material alone can be determined and can be used for recognizing the material.

The time shift or phase shift and the damping are advantageously determined by way of the receive signal being compared to a comparison signal which was produced in the same manner, without the object being located in the beam path between the THz emitter and the phase-sensitive THz receiver and being beamed through by the THz radiation.

In one advantageous development, the THz radiation which is produced by the THz emitter and detected by the phase-sensitive THz receiver contains further frequency components, for which likewise the time shift or phase shift and/or the damping or absorption of the receive signal is determined. A greater accuracy can be achieved by way of this. The different frequency components of the THz radiation can be emitted and detected at the same time or successively, independently of their number, wherein with a simultaneous detections one can effect a signal separation e.g. with the help of different modulation frequencies for the different frequency components.

For producing the different frequency components, the device used as a light source for activating the THz emitter as well as the phase-sensitive THz receiver can include two or more lasers which are detuned or detuneable to one another by the desired magnitude of the THz beat frequency. For example, two lasers, of which one is switched over between two frequencies, can be provided for a sequential measurement of the two frequency components. Instead of this, one can also provide three lasers which are detuned with respect to one another and which permit a simultaneous measurement of two or three frequency components produced by way of this. Thereby, beat frequencies between the different lasers correspond in each case to the arising THz frequencies. For this, the laser powers of the different lasers can be modulated differently for a simultaneous measurement of different frequency components.

In advantageous embodiments, a synchronization function or synchronization connection between the THz emitter and the phase-sensitive THz receiver exists, so that a stable common time base is ensured for the detection of the time position or phase.

A common light source for activating the THz emitter as well as the THz receiver can be provided for the synchronization of the phase-sensitive THz receiver with the THz emitter. This light source can e.g. be connected via glass fibers or other waveguides to the THz emitter and to the phase sensitive THz receiver. The THz emitter can be a photoconductor or a photodiode with an integrated antenna, while the phase-sensitive THz receiver can be given by a photoconductor which is sensitive if possible to light of the same wavelength and having an integrated antenna.

Thereby, a variable, optical delay circuit can be connected between the light source and the phase-sensitive THz receiver or between the light source and the THz emitter, for measuring the time shift or phase shift.

The THz emitter and the phase-sensitive THz receiver of the device should be arranged such that the object to be examined can be arranged in a beam path between the THz emitter and the phase-sensitive THz receiver. For this, the object can be arranged spatially between the THz emitter and the phase-sensitive THz receiver or also between a mirror on one side and the THz emitter and the phase-sensitive THz receiver on the other side. In the latter mentioned case, the THz radiation enters twice through the object and thereby typically penetrates fourfold the wall thickness of the object. In each case, lenses for collimation or focussing the THz radiation can be provided between the THz emitter and the object to be examined, as well as between this object and the phase-sensitive THz receiver. These lenses can be given by e.g. cylinder lenses inasmuch as bottles or similarly shaped and roughly cylindrical objects are to be examined, and by way of this one succeeds in the THz radiation entering through a wall of the object in each case in an quite accurately perpendicular manner.

A particularly precise examination and assignment of the material is possible in an embodiment of the method, with which the THz emitter emits the THz radiation in the form of at least one pulse which necessarily contains a multitude of different frequencies. In this case, the device, as a light source for activating the THz emitter and the phase-sensitive THz receiver can in particular include a pulse laser.

Inasmuch as the examined object is beamed through with a THz pulse, the time shift and the damping or absorption can be determined e.g. for a maximal amplitude of the receive signal produced by the THz pulse. Since several frequency components go into the maximal amplitude and its temporal position, a special case of the previously described method is realized by way of this. The time shift can of course also be determined by way of a position of a defined flank of a receive signal.

An even more accurate evaluation is possible if the receive signal produced by the pulse is subjected to a Fourier transformation, wherein the damping or absorption is determined in a frequency-dependent manner after carrying out the Fourier transformation. On the other hand, for determining the time shift, in this case too, preferably the receive signal is used in its form before the Fourier transformation. Of course the Fourier transformation can also be replaced by other types of frequency analysis.

BRIEF DESCRIPTION OF THE FIGURES

Embodiment examples of the invention are hereinafter explained by way of the FIGS. 1 to 4.

DETAILED DESCRIPTION

Figure 1:
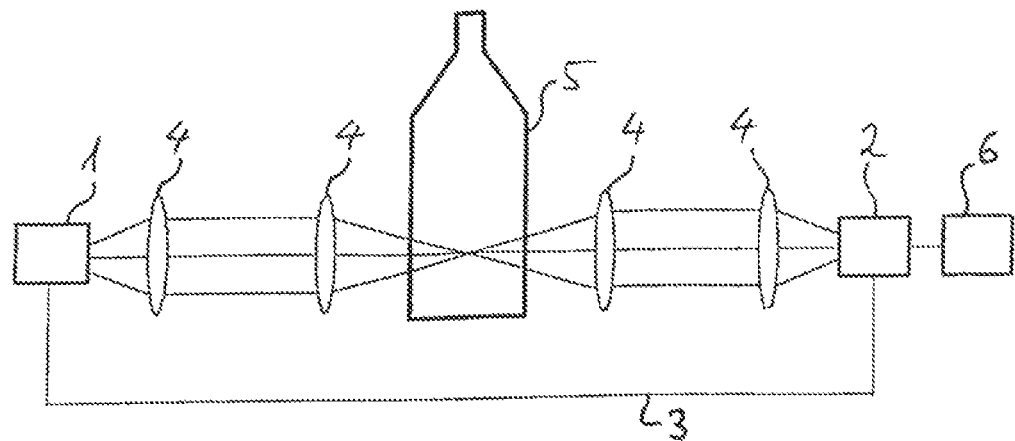
FIG. 1 is a schematic representation of a device for identifying a material, from which an empty container is manufactured.

The device shown in FIG. 1 includes a THz emitter 1 for producing THz radiation of at least two different frequency components, as well as a phase-sensitive THz receiver for detecting the time position/phase and power/amplitude of this THz radiation. The phase-sensitive receiver 2 is connected to the THz emitter 1 via a synchronization function—represented here as a synchronization lead 3—in order to permit an as time-precise as possible phase-sensitive detection of the THz radiation produced by the THz emitter 1, by way of the phase-sensitive THz receiver 2. This synchronization lead 3 can e.g. be a light guide, by way of which the THz emitter 1 as well as the phase-sensitive THz receiver 2 can be activated by a common light source 2. Lenses 4 which are only represented schematically are arranged between the THz emitter 1 and the phase-sensitive THz receiver 2, and these lenses form THz imaging optics and collimate and focus the THz radiation such that a plastic bottle 5 arranged in a beam path between the THz emitter 1 and the phase-sensitive THz receiver 2 is beamed through with THz radiation. Finally, the device shown in FIG. 1 includes an evaluation unit 6 which simultaneously serves as a control unit for the THz emitter 1 and the phase-sensitive THz receiver.

Now, at least for a first frequency component of the THz radiation which has a frequency of 0.1 THz for example, a time shift or phase shift of a receive signal which is caused by the plastic bottle 5 is measured with this device, whereby this receive signal is produced by the THz radiation in the phase-sensitive THz receiver 2. A weakening or damping of the signal which is caused by the plastic bottle 5 is determined at least for a higher-frequency second frequency component of the THz radiation with a frequency of 1 THz for example. The time shift or phase shift and the damping or weakening is thereby determined by way of the receive signal being compared to a comparison signal which is produced in the same manner, before the plastic bottles 5 is placed in the device or after the plastic bottle 5 is removed from the device.

The evaluation unit 6 by way of programming technology, amid the assumption of a refractive index of for example n=1.62 which is typical for plastics, is set up to at least approximately determined a material thickness of this plastic bottle 5 which corresponds to twice a wall thickness of this plastic bottle 5, since the THz radiation penetrates a wall of the plastic bottle 5 at two locations. A wavelength of the first frequency component of the THz radiation is thereby so large, that the measured phase shift unambiguously permits the material thickness to be unambiguously deduced. Moreover, the evaluation unit 6 is programmed such that in dependence on the determined material thickness and the measured damping or weakening, it computes an absorption coefficient of the material forming the plastic bottle 5, at least for the mentioned second frequency component of the THz radiation.

Figure 2:
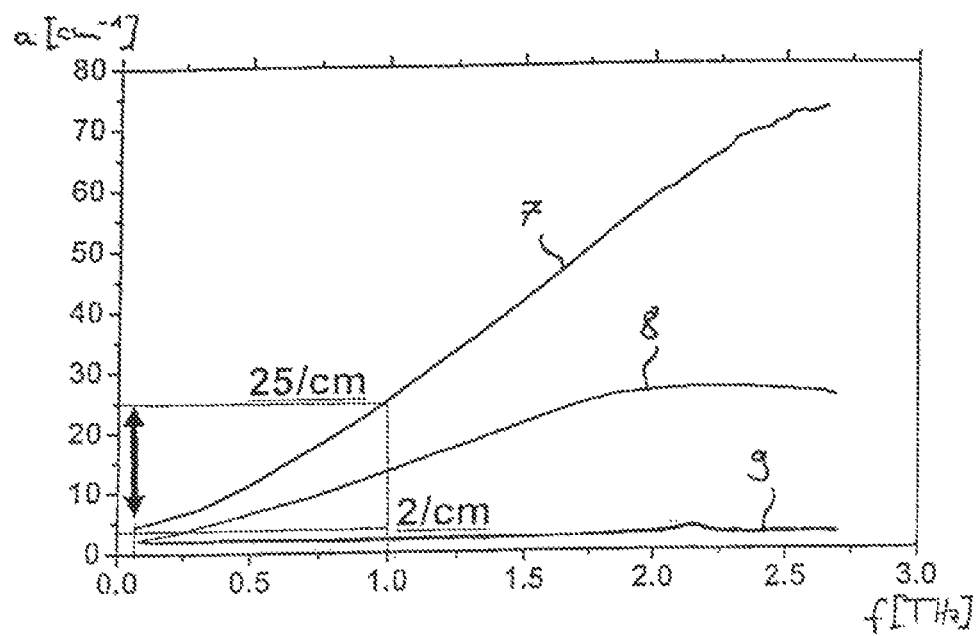
FIG. 2 is a diagram illustrating a frequency dependence on absorption coefficients of different plastics for THz radiation.

FIG. 2 illustrates as to how by way of this, it is possible to deduce the material from which the plastic bottle 5 at least mainly consists. Thereby it is of no significance if the plastic bottle 5 is provided with paper labels, since paper is almost completely transparent with regard to THz radiation. Frequency dependencies of absorption coefficients a for different plastics are illustrated in FIG. 2. A course 7 of the absorption coefficient for PET (polyethylene terephthalate) a corresponding course 8 for PC (polycarbonate) and a course 9 of the absorption coefficient of HDPE (polyethylene of high density with a weakly branched polymer chain) are shown individually there.

As is to be recognized in FIG. 2, these plastics for an electromagnetic radiation of a frequency of 0.1 THz in each case still have a very low absorption coefficient, so that the time shift or phase shift caused by the plastic bottle 5 can be comfortably measured for the frequency component of this frequency. With the frequency of the second frequency component of 1 THz, the different plastics on the other hand display larger differences, wherein PET has an absorption coefficient of about 25 $cm^{-1}$ at this frequency, and HDPE an absorption coefficient of only about 2 $cm^{-1}$ at the same frequency. If now by way of measuring the time shift or phase shift for the first frequency component, the material thickness is determined at least approximately and therefore the absorption coefficient for the second frequency components can be determined with a similar accuracy, then the differences in the absorption behavior which are shown in FIG. 2 therefore already permit a very reliable decision as to the type of plastic the material forming the plastic bottle 5 is. If the time shift or phase shift with the described method is additionally determined for the second frequency component, then the material thickness can be determined in an even more precise manner. Since the weakening of the receive signal by way of the plastic bottle 5 is not exclusively caused by an absorption by the plastic forming the plastic bottle 5, but also partly by way of reflections and scatter which in turn are caused by a roughness of the surface or contamination of the plastic bottle 5, the damping or weakening of the receive signal is also additionally determined for the first frequency component, so that a frequency-independent component of the weakening which is illustrated in FIG. 2 by the double arrow can be determined, and this component is then only insignificantly influenced by the other mentioned losses, since these—thus reflections and scatter by way of surfaces, roughness or contamination—are practically frequency-independent. Finally, it is of course also possible for the THz radiation which is produced by the THz emitter 1, to contain further frequency components, for which the time shift or phase shift and the damping or weakening of the receive signal is likewise determined and correspondingly evaluated.

Thus the material forming the plastic bottle 5 can be identified or at least assigned to a group of possible materials by way of a suitable programming of the evaluation unit 6, by way of the computed absorption coefficient or a frequency-dependent component of the absorption coefficient which is determined therefrom, being compared to comparison values, wherein a preliminary decision or a supplementary decision as to which material it is a case of, can be made already on account of the at least approximately determined material thickness. Thereby, one can utilize a prior knowledge with regard to the material thicknesses with the objects of the examined type for certain materials.

Figure 3:
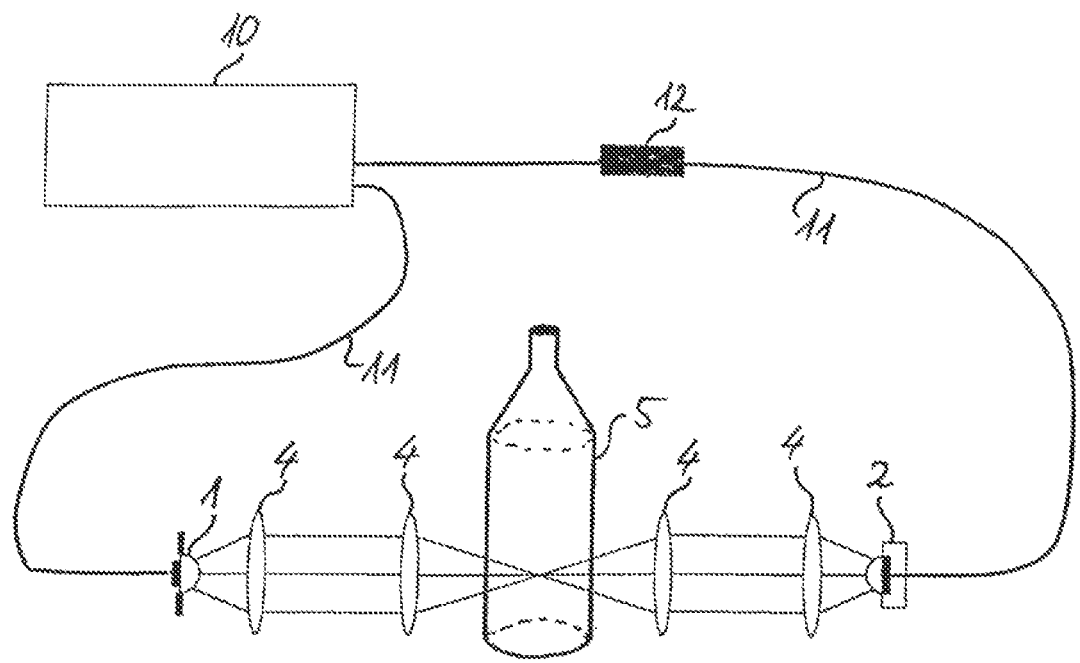
FIG. 3 is a schematic representation of important components of an embodiment of a device of the type shown in FIG. 1.

A few components of a device of the type already described by way of FIG. 1 are represented in a more detailed manner in FIG. 3. Recurring features are thereby again provided with the same reference numerals. Here, one can recognize a laser light source 10 which serves for activating the THz emitter 1 as well as the phase-sensitive THz receiver 2. Thereby, the phase-sensitive THz receiver 2 is realized by way of a photoconductor with an integrated antenna which is sensitive to light which is produced by the laser light source 10, while the THz emitter 1 is given by a corresponding photoconductor or by a photodiode with an integrated antenna and which is sensitive to light of the same wavelength. The laser light source 10 is optically coupled in each case via a glass fiber 11 to the THz emitter 1 and the phase-sensitive THz receiver 2. A variable optical delay circuit 12 is connected in a course of one of these glass fibers 11 for measuring the time shift or phase shift. The lenses 4 can be advantageously designed as cylinder lenses which have an axis of symmetry running parallel to an axis of symmetry of the plastic bottle 5, so that the THz radiation can be led such that it penetrates a wall of the plastic bottle 5 in each case in a perpendicular manner.

The laser light source 10 can e.g. include two lasers which are slightly detuned to one another, of which one has an adjustable resonant frequency. Thereby, these lasers are detuned to on another such that a beat frequency lies in the THz range and corresponds to one of the THz frequencies to be produced. The THz emitter 1 and the phase-sensitive THz receiver 2 are then activated with this beat frequency. The two different frequency components of the THz radiation are then produced by way of switching over the one laser between two slightly different resonant frequencies. Instead of this, the laser light source 10 can also e.g. include three lasers each with resonant frequencies which are slightly detuned to one another, so that several beat frequencies arise and accordingly the different frequency components of the THz radiation are produced simultaneously. Then an output power of the different lasers can be modulated in a different manner for a simultaneous detection of the different frequency components.

Figure 4:
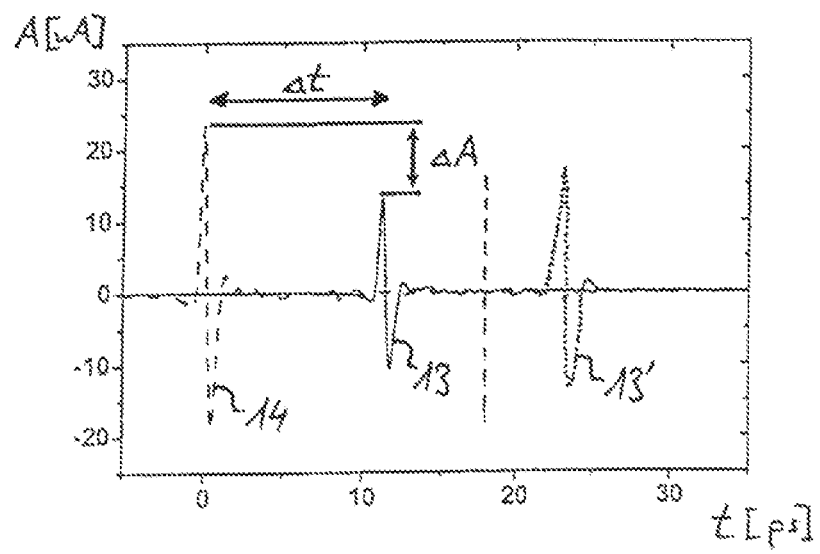
FIG. 4 is a diagram which illustrates how a THz pulse which is produced and detected with this device is influenced in a different manner by way of empty container of a different type.

In another embodiment, the laser light source 10 is given by a pulse laser which leads to the THz emitter 1 emitting the THz radiation in the form of one or more pulses which each contain a complete spectrum of many different frequency components. In FIG. 4, it is shown what a receive signal 12 produced in the phase-sensitive THz receiver 2 looks like if the plastic bottle 5 is a returnable bottle manufactured from PET. The receive signal 13 is offset by a time shift $\Delta t$ with respect to a comparison signal 14 which is produced in the same manner when the plastic bottle 5 is not located between the THz emitter 1 and the phase-sensitive THz receiver 2, wherein an amplitude A of the receive signal 13 turns out to be lower than an amplitude of the comparison signal 14 by a weakening $\Delta A$. The time shift $\Delta t$ is thereby determined with the help of the variable optical delay circuit 12. The material thickness is determined from the time shift $\Delta t$ by the evaluation unit 6 which is not drawn in FIG. 3, and this material thickness with the arrangement of FIG. 3 corresponds to double the wall thickness of the plastic bottle 5, wherein moreover the absorption coefficient of the material forming the plastic bottle 5 is determined in dependence on the thus determined material thickness and the weakening $\Delta A$, wherein the thus determined absorption coefficient can be burdened by inaccuracies which can be due to contamination or roughness of the material. A contribution of reflections to the weakening $\Delta A$ on the other hand can be eliminated in a numeric manner. The thus determined absorption coefficient is moreover to be assigned to a frequency component which dominates the maximal amplitude of the pulse produced by the laser light source 10.

For comparison, a different receive signal 13' is drawn in FIG. 4 and is then obtained with a corresponding measurement of the plastic bottle 5 manufactured of HDPE and having thicker walls. Since HDPE vessels typically have a greater wall thickness than bottles of PET, on the basis of differences in the time shift $\Delta t$, one can already make a preliminary decision as to the type of material or to what type of plastic bottle 5 it is the case of Thus e.g. a time shift $\Delta t$ of more than the 18 picoseconds indicated in FIG. 4 by a vertical dashed line can serve as an indication for a HDPE empty, while a shorter time shift $\Delta t$ tends to indicate PET. In a similar manner, one can also differentiate between returnable bottles and disposable bottles with some certainty, since disposable bottles are typically designed with thinner walls.

For identifying the material forming the plastic bottle 5, the evaluation unit 6 can thus be set up by way of programming technology, to compare the at least approximately determined material thickness and the computed absorption coefficient or a variable derived therefrom, in each case with comparison values and to assign the plastic bottle 5 through which the THz radiation is beamed, to a material or a group of materials or to a certain bottle type, if the material thickness or the absorption coefficient or the variable derived therefrom in each case fall into an interval assigned to the material or the group of materials or to the bottle type. This is possible with a high degree of certainty if only a limited number of materials are to be considered, for example glass, PET or HDPE.

Finally, the evaluation unit 6 can also be set up to subject the produced receive signal 13 or 13' to a Fourier transformation and to determine the weakening caused by the plastic bottle 5 in a frequency-dependent manner. Then a very accurate evaluation of the material forming the plastic bottle is also possible if the weakening is amplified e.g. on account of surface roughness or due to a contamination of the plastic bottle 5.

Concluding, one can thus ascertain that beaming with a THz pulse through an object which in the present case is given by the plastic bottle 5, is an advantageous special case of a use of a multitude of different frequency components, with which the thickness measurements and absorption measurements can be refined. Inasmuch as different discrete frequency components are used, it is advantageous if one of the frequency components serves for carrying out a reference measurement, with which the absorption by the material is still very low, but the unspecific disturbance effects however are already taken into account. This reference measurement can be effected e.g. with a relatively small frequency of between 50 GHz and 0.3 THz. One advantageous design of the method envisages a first assignment to a material or a group of materials and/or to a bottle or vessel type being effected on the basis of the determined material thickness, by way of the determined material thickness being compared to values from a data bank. Then a second assignment of the material and of the bottle type results from a comparison of the absorption behavior observed in particular at higher frequencies, with comparison values from the data bank.

With a typically design of the suggested method, the empties, for example bottles are thus beamed through with THz waves, wherein firstly the phase shift or time delay which is effected by way of this is measured. A thickness measurement on the basis of this phase shift or time delay and amid the assumption of an average refractive index thus provides a very rapid first allocation and separation of the basic bottle types into valuable PET material and less valuable other plastics. Thus in particular disposable drinks containers, returnable drinks containers and other cheaper plastics can be differentiated from one another. Glass bottles are significantly thicker than plastic bottles and therefore can likewise be easily differentiated. Metals in contrast are not transparent to THz radiation and can therefore be likewise well differentiated. The result of the thickness measurement then also serves as an input value for the computation of the expected amplitude damping. Damping measurements in contrast would not provide valuable information and cannot be usefully utilised without any knowledge of the material thickness. Apart from the refractive indexes n, the absorption coefficients a in the THz range are known or can be determined, for the different materials of interest. For this reason, the expected reflection losses $$R=(n_1-n_2)^2/(n_1+n_2)^2$$

at the surfaces, and the absorption losses dependent on the thickness and which includes the product of the material thickness and absorption coefficient, can be computed. The expected losses can then be compared to the measured amplitude ratio of the pulses or frequency components with a bottle and without a bottle in the beam path. A second material assignment thus results, with which the first assignment can be checked.

A critical point with regard to amplitude evaluation is the fact that an additional damping can be effected due to rough surfaces and contaminated bottles. This can be detected for a more accurate examination and the measurement signal corrected with respect to these disturbances. The disturbances can be detected by way of measurements at relatively low frequencies, with which almost no absorption occurs in the material, but the disturbance effects are however almost identical as with higher frequencies which serve for the absorption measurement. The difference of the dampings at the different frequencies thus with a high precision results in a purely material damping which permits the material to be deduced. The absorption coefficient can then be computed taking into account the previously determined material thickness. Finally, the plastic or the other material is identified by way of comparison of the absorption coefficients with a data bank, and then with typically designs of the method are then led to the corresponding recycling path.

The invention claimed is:

1. A method of identifying a material from a class of materials that are transparent to THz radiation, the method comprising:
producing THz radiation via a THz emitter, the THz radiation simultaneously or sequentially containing at least one first frequency component and a second frequency component of a wavelength which is different from the first frequency component, wherein absorption of the first frequency component of the THz radiation is lower than absorption of the second frequency component of the THz radiation for each one of the materials of the class of materials;
beaming the THz radiation through an object which is at least partly formed from the material to be identified;
detecting THz radiation exiting the object with a phase-sensitive THz receiver, wherein the THz radiation exiting the object produces a receive signal in the phase-sensitive THz receiver;
measuring, at least for the first frequency component of the THz radiation, a time shift or phase shift of the receive signal, the time shift or phase shift being caused by the object;
determining a measure of a material thickness of the object from the time shift or the phase shift;
determining, for the first frequency component of the THz radiation, a first damping component of a damping of the receive signal and, for the second frequency component of the THz radiation, a second damping component of the damping of the receive signal, the damping of the receive signal being caused by the object;
computing a difference between the first damping component and the second damping component; and
computing a frequency-dependent component of an absorption coefficient for the second frequency component based on the difference between the first and second damping component and the determined measure for the material thickness.

2. The method of claim 1, wherein the phase-sensitive THz receiver is synchronized with the THz emitter via at least one of a synchronization connection and a common light source.

3. The method of claim 1, wherein the object is a bottle or other non-organic vessel.

4. The method of claim 1, wherein the class of materials is a class consisting of plastic materials.

5. The method of claim 1, wherein a wavelength of the first frequency component is selected at least as large as a wall thickness of the object and the wavelength of the second frequency component is selected smaller than the wavelength of the first frequency component.

6. The method of claim 1, further comprising measuring the time shift or phase shift of the receive signal for the second frequency component.

7. The method of claim 1, wherein the time shift or phase shift and the damping are determined by comparing the receive signal to a comparison signal which is produced in the same manner, without the object being beamed through.

8. The method of claim 1, wherein the THz radiation contains further frequency components, and the method further comprises measuring the time shift or phase shift and/or determining the damping of the receive signal.

9. The method of claim 1, wherein the THz emitter emits the THz radiation in the form of at least one pulse.

10. The method of claim 9, wherein the time shift and the damping are determined for a maximal amplitude of the receive signal produced by the pulse.

11. The method of claim 9, wherein the receive signal produced by the pulse is subjected to a Fourier transformation, wherein the damping is determined in a frequency-dependent manner after the Fourier transformation.

12. The method of claim 1, further comprising identifying the material or assigning the material to a group of possible materials by comparing the frequency-dependent component of the absorption coefficient to comparison values.

13. The method of claim 12, wherein a preliminary decision or supplementary decision as to which materials or groups of materials are considered is made using the determined measure for the material thickness.

14. A device for identifying a material from a class of materials which are transparent to THz radiation, the device comprising:
- a THz emitter for producing THz radiation with simultaneously or sequentially at least one first frequency component and a second frequency component of a wavelength which is different therefrom, wherein absorption of the first frequency component of the THz radiation is lower than absorption of the second frequency component of the THz radiation for each one of the materials of the class of materials;
- a phase-sensitive THz receiver for detecting the THz radiation and for generating a receive signal in response to the detected THz radiation; and
- an evaluation unit which is configured to measure a time shift or phase shift of the receive signal produced by the THz radiation in the phase-sensitive THz receiver, at least for the first frequency component and is configured to determine an amplitude of the receive signal or at least one component of the receive signal which corresponds to the second frequency component;
- wherein the evaluation unit is programmed to determine a measure for a material thickness of a beamed-through object from the time shift or phase shift and to determine, for the first frequency component of the THz radiation, a first damping component of a damping of the receive signal and, for the second frequency component of the THz radiation, a second damping component of the damping of the receive signal, the damping of the receive signal being caused by the object, from the measured amplitude, to calculate the difference between the first damping component and the second damping component, and to compute a frequency-dependent component of an absorption coefficient based on the calculated difference between the first and second damping components and the determined measure for the material thickness.

15. The device of claim 14, further comprising a synchronization connection between the THz emitter and the phase-sensitive THz receiver, for synchronizing the phase-sensitive THz receiver with the THz emitter.

16. The device of claim 14, wherein the evaluation unit is programmed to compare the computed absorption coefficient or a variable derived therefrom with comparison values, and to assign the beamed-through object to a material or to a group of possible materials if the absorption coefficient or the variable derived therefrom falls in an interval assigned to the material or to the group of materials.

17. The device of claim 14, further comprising a common light source for activating the THz emitter as well as the phase sensitive THz receiver.

18. The device of claim 17, wherein the light source comprises a pulse-laser or at least two lasers which are detuned to one another or can be detuned to one another.

19. The device of claim 14, further comprising a variable optical delay circuit connected between the light source and the phase-sensitive THz receiver or between the light source and the THz emitter, for measuring the time shift or phase shift.

20. The method of claim 1, wherein the first and second frequency components of the THz radiation consist of electromagnetic waves, the frequencies of the electromagnetic waves of the first frequency component being smaller than the frequencies of the electromagnetic waves of the second frequency component.

21. The method of claim 20, wherein the first frequency component of the THz radiation consists of electromagnetic waves with frequencies between 50 GHz and 200 GHz, and/or wherein the second frequency component of the THz radiation consists of electromagnetic waves with frequencies between 0.5 THz and 4 THz.

22. The method of claim 12, further comprising the step of:
- selecting, from a variety of different recycling paths of a recycling process, a recycling path for the object, the selected recycling path depending on the identified material of the body.

23. The device of claim 14, wherein the evaluation unit is programmed to identify the material or to assign the material to a group of possible materials by comparing the computed frequency-dependent component of the absorption coefficient to comparison values, wherein the evaluation unit is configured to select, depending on the identified material of the object, a recycling path for the body from a variety of different recycling paths of a recycling process.

* * * * *